United States Patent [19]

Schreiber et al.

[11] Patent Number: 4,519,101

[45] Date of Patent: May 28, 1985

[54] JOINT SOCKET

[75] Inventors: Adam Schreiber, Kusnacht; Jacob Hilaire, Winterthur, both of Switzerland

[73] Assignee: Sulzer Brothers Limited, Winterthur, Switzerland

[21] Appl. No.: 454,987

[22] Filed: Jan. 3, 1983

[30] Foreign Application Priority Data

Jan. 8, 1982 [CH] Switzerland .................. 91/82

[51] Int. Cl.³ .................................. A61F 1/04
[52] U.S. Cl. ............................. 3/1.912; 3/1.91; 128/92 C; 128/92 CA
[58] Field of Search .......... 128/92 C, 92 CA; 3/1.91, 1.912, 1.913

[56] References Cited

U.S. PATENT DOCUMENTS 4,068,324  1/1978  Townley et al. .......... 128/92 C
4,180,873  1/1980  Fixel .......................... 128/92 C
4,385,405  5/1983  Teinturier .................. 3/1.912

FOREIGN PATENT DOCUMENTS 2416004  8/1979  France ....................... 3/1.912

Primary Examiner—Richard J. Apley
Assistant Examiner—David J. Isabella
Attorney, Agent, or Firm—Kenyon & Kenyon

[57] ABSTRACT

The joint socket consists of two parts, namely an outer split sleeve and a conical insert. The conical insert contains a hemispherical socket for receiving a joint head. The outer surface of the sleeve is in the form of a truncated cone and is provided with depressions and ribs as well as longitudinal grooves. The ribs serve to penetrate into an artifically created socket bearing of a bone to insure a secure primary fixation in a cement-free anchorage. A firm securement of the socket is insured by the expansion of the sleeve and the penetration of the ribs into the bone.

10 Claims, 2 Drawing Figures

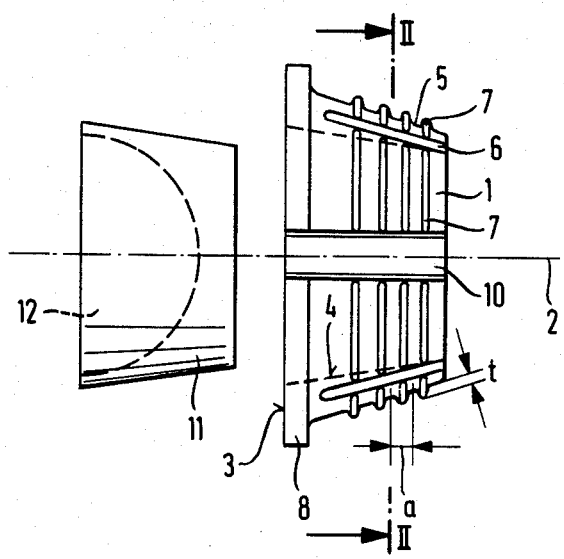
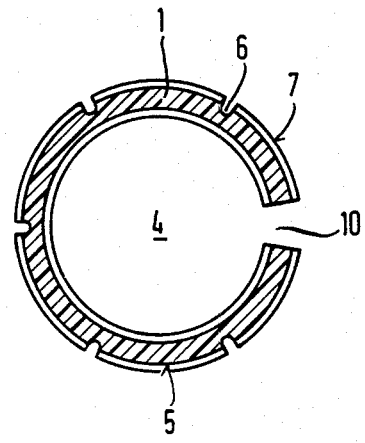

JOINT SOCKET

This invention relates to a joint socket. More particularly, this invention relates to a joint socket for anchoring in a bone in a cement-free manner. Still more particularly, this invention relates to a joint socket for a hip joint prosthesis.

As is known, various types of artificial joint sockets have been known which can be anchored, for example in a pelvis, in a cement-free manner. For example, Swiss Pat. No. 568,735 describes a joint socket which has an exterior shape in the form of a rotation-symmetric truncated cone. Generally, the form of a truncated cone was chosen because sockets having a hemispherical shape were found to push out of their anchorage relatively easily, particularly in a cement-free anchorage. This pushing out was found to be caused by elastic deformations caused by alternating stress and relief of the pelvis bone. This occurred even if the external hemispherical surface of the socket were provided with circular ribs and depressions which may or may not be interrupted by grooves disposed along a generatrix, as described in French Pat. No. 2,301,217.

In order to fix these known truncated cone sockets, use has been made of a thread which is cut into the surface of the truncated cone. This permits the socket to be screwed into a corresponding thread in an artificially created socket bearing of a pelvis bone. In practice, however, the fixation of a socket by means of a thread has proven to be disadvantageous. This is because it is difficult to cut a thread in a surgically prepared socket bearing in the pelvis bone with the precision required for a cement-free fixation. Further, there is a danger that the thread cut into the relatively soft bone becomes damaged or destroyed by "over cutting" of the tap.

Accordingly, it is an object of the invention to provide a joint socket which can be anchored in a cement-free manner without the need for cutting a thread in a bone.

It is another object of the invention to provide a joint socket which can be firmly seated in a surgically prepared bone without the use of cement.

It is another object of the invention to provide a joint socket for a hip joint prosthesis which can be anchored in place in a relatively easy manner.

Briefly, the invention provides a joint socket for anchoring in a bone in a cement-free manner which is comprised of a longitudinally split sleeve of truncated conical shape and a conical insert. The sleeve is provided with a plurality of circumferential depressions which define a plurality of circumferentially projecting ribs on an outer surface, a plurality of longitudinally disposed grooves in the outer surface and an internal cavity of conical shape. The conical insert is sized to fit into the cavity in the sleeve in wedging relation and has an internal socket for receiving a joint head.

In order to fix the joint socket, a socket bearing can be surgically prepared within a bone, such as a pelvis, without the need for a thread. The socket bearing may be produced, for example by mill-cutting. The sleeve can then be simply inserted in the bearing in the direction of the axis of the sleeve. In this regard, the sleeve has a diameter which can be slightly reduced due to the split by compression in the circumferential direction by about two millimeters. Advantageously, the sleeve is elastic in the circumferential direction. After the sleeve has been put in place, the conical insert is inserted into the cavity of the sleeve by pressing or light hammering. This results in an expansion of the split sleeve causing the ribs on the sleeve to "penetrate" into the wall of the socket bearing.

Thus, a so-called primary fixation is insured by which the socket is held in place until tissue has grown into or about the depressions on the socket. In this regard, the longitudinal grooves which are formed in the socket serve to prevent rotation of the socket. Advantageously, these grooves protrude into the sleeve more deeply than the depressions.

The adhesion of the insert in the inner cavity of the sleeve can be improved if both components are self-locking.

The sleeve may also be provided with an abutment collar at the wide end in order to prevent too deep a pressing or penetrating of the socket into the bone.

The socket may be made of any suitable materials which are used for implants. For example, the sleeve may be made of a polyethylene selected from the classification of HDPE and UHMW. Further, the depressions may be of a depth of from 1 to 4 millimeters with a spacing from base to base of from 2 to 5 millimeters.

Although stable plastics which are tolerated by the body are preferred materials, the sleeve may alternatively be made of a metal or metal alloy which is customary in implant technology. For the inserts, all materials which are customarily suitable for implant technology are suitable, that is plastics, metal, metal alloys and bioceramic materials.

These and other objects and advantages of the invention will become more apparent from the following detailed description taken in conjunction with the accompanying drawings wherein:

FIG. 1 illustrates a side view of the components of a joint socket constructed in accordance with the invention; and FIG. 2 illustrates a view taken on line II—II of FIG. 1.

Referring to FIG. 1, the joint socket, for example for a hip joint prosthesis, is constructed of a sleeve 1 and a conical insert 11.

Referring to FIGS. 1 and 2, the sleeve 1 is of truncated conical shape which is symmetric about an axis of rotation 2. The sleeve 1 includes a longitudinal split 10 which has a minimum width great enough for the sleeve diameter to be elastically reduced by several millimeters by circumferential compression. As indicated, the sleeve 1 has a plurality of circumferential depressions 5 machined in the outer surface in order to define a plurality of circumferentially projecting ribs 7. In addition, the outer surface of the sleeve 1 is provided with a plurality of longitudinally disposed grooves 6 which are provided to prevent rotation of the sleeve 1 when in place in a bone.

Depending on the material, the height and spacing of the ribs 7 are selected so that at least some of the ribs 7 become elastically deformed when the sleeve 1 is pressed into a prepared pelvis bone. These ribs thus form a barb-type anchorage on the bone wall in order to promote a primary fixation.

In addition, the sleeve 1 has an abutment collar 8 at the wise end which projects radially outwardly of the axis 2. This collar 8 serves as an abutment to limit the insertion of the sleeve 1 into a bone. The sleeve 1 also includes an internal cavity 4 of conical shape and which is coaxial with the outer surface of the sleeve.

Referring to FIG. 1, the conical insert 11 is sized to fit into the cavity 4 of the sleeve 1 in wedging relation. In addition, the insert 11 has an internal socket 12 of hemispherical shape for receiving a joint head, for example of a femur prosthesis (not shown). This socket 12 may be machined in at the wide end coaxially on the axis 2.

The components 1, 11 of the joint socket can be made of polyethylene, for example of the classification HDPE or the classification UHMW.

As indicated in FIG. 1, the depth t of the depressions 5 is, for example in a range of from 1 to 4 millimeters, and preferrably two millimeters while the spacing (pitch) a, measured from base to base, is in the range of from 2 to 5 millimeters, and preferably 3 millimeters. The half cone angle of the insert 11 as well as the inner cavity 4, as measured relative to the axis of rotation 2, is self-retaining and has a value of 5°.

In order to implant the socket, it has been found desirable to provide a recess in the bone which is adapted for an exact fit to the sleeve 1 as to form and dimensions. The recess may even be a little narrower than the outer form of the "relaxed" i.e. uncompressed, sleeve 1. Thereafter, the sleeve 1 is compressed and inserted into the recess. Next, the conical insert 11 is pressed into the cavity 4 and hammered in lightly. The resulting wedging action of the insert 11 causes the sleeve 1 to be expanded and pressed via the ribs 7 into the bone recess.

Since the form of the entire socket joint, including that of the actual socket 12, is completely rotation-symmetric the socket can be rotated about the axis 2 at will when being implanted and can be inserted without observing a certain position, for example, a marked point on the edge of the sleeve 1 relative to a reference point on the pelvis bone. This provides a further advantage of the socket.

The expansion of the split sleeve as well as the form of the generated surface of the sleeve 1 insures a secure primary fixation of the socket in a bone. Further, since the sleeve is by construction open at opposite ends, the disadvantage of a limited penetration depth of the insert is not present. In this respect, the split in the sleeve permits a radial expansion of the sleeve. The truncated conical form of the socket also permits a large area support in the bone which can, to a large extent, follow the elastic deformations of the pelvis during stress and relief.

What is claimed is:

1. A joint socket for anchoring in a bone in cement-free manner; said joint socket comprising
    a longitudinally split sleeve of truncated conical shape open at opposite ends to permit radial expansion, said sleeve having a plurality of circumferential depressions defining a plurality of circuumferentially projecting ribs on an outer surface, a plurality of longitudinally disposed grooves in said outer surface and an internal cavity of conical shape; and
    a conical insert sized to fit into said cavity of said sleeve in wedging relation and having an internal socket for receiving a joint head.

2. A joint socket as set forth in claim 1 wherein said sleeve and said insert are self-locking.

3. A joint socket as set forth in claim 1 wherein said depressions are of a sufficient depth and spacing to permit said ribs to penetrate into an implanted bone.

4. A joint socket as set forth in claim 3 wherein said sleeve is made of polyethylene selected from the classifications of HDPE and UHMW and said depressions have a depth of from 1 to 4 millimeters and a spacing of from 2 to 5 millimeters.

5. A joint socket as set forth in claim 1 wherein said sleeve includes an abutment collar at a wide end thereof.

6. A joint socket as set forth in claim 1 wherein said sleeve is elastically deformable in a circumferential direction.

7. A joint socket as set forth in claim 1 wherein said grooves penetrate deeper into said sleeve than said depressions.

8. A joint socket for a hip joint prosthesis, said socket comprising
    a longitudinally split sleeve of truncated conical shape open at opposite ends to permit radial expansion, said sleeve having a plurality of circumferentially projecting ribs on an outer surface, and an internal cavity of conical shape; and
    a conical insert sized to fit into said cavity of said sleeve in wedging relation and having an internal socket for receiving a joint head.

9. A joint socket as set forth in claim 8 wherein said sleeve has circumferential depressions defining said ribs, each said groove having a greater depth than said depressions.

10. A joint socket as set forth in claim 9 wherein said depressions have a depth of from 1 to 4 millimeters and a spacing of from 2 to 5 millimeters.

* * * * *

UNITED STATES PATENT AND TRADEMARK OFFICE
CERTIFICATE OF CORRECTION

PATENT NO. : 4,519,101

DATED : May 28, 1985

INVENTOR(S) : Adam Schreiber and Jacob Hilaire

It is certified that error appears in the above—identified patent and that said Letters Patent is hereby corrected as shown below:

Column 2, line 64 change "wise" to -wide-

Column 4, line 6 change "circuumfer-" to -circumfer- -

Signed and Sealed this

Twenty-ninth Day of October 1985

[SEAL]

Attest:

DONALD J. QUIGG

Attesting Officer

Commissioner of Patents and
Trademarks—Designate